United States Patent
Schütze et al.

(10) Patent No.: US 7,848,552 B2
(45) Date of Patent: Dec. 7, 2010

(54) METHOD FOR PROCESSING A MATERIAL BY MEANS OF A LASER IRRADIATION AND CONTROL SYSTEM

(75) Inventors: Karin Schütze, Tutzing (DE); Bernd Sägmüller, Weilheim i. (DE); Thomas Rheingans, Wackersberg (DE)

(73) Assignee: P.A.L.M. Microlaser Technologies GmbH, Bernried (DE)

( * ) Notice: Subject to any disclaimer, the term of this patent is extended or adjusted under 35 U.S.C. 154(b) by 1061 days.

(21) Appl. No.: 11/558,167

(22) Filed: Nov. 9, 2006

(65) Prior Publication Data

US 2007/0160280 A1 Jul. 12, 2007

Related U.S. Application Data

(63) Continuation of application No. PCT/EP2005/003344, filed on Mar. 30, 2005.

(51) Int. Cl.
- G06K 9/00 (2006.01)
- G06K 9/46 (2006.01)
- B23K 26/00 (2006.01)
- A62B 1/04 (2006.01)

(52) U.S. Cl. .................. 382/128; 382/141; 382/203; 219/121.6; 348/67

(58) Field of Classification Search .......... 382/100, 382/128–132, 141, 203, 204; 219/121.6–121.86; 348/67

See application file for complete search history.

(56) References Cited

U.S. PATENT DOCUMENTS

| | | | |
|---|---|---|---|
| 4,523,278 A | 6/1985 | Reinhardt et al. | 364/413 |
| 4,682,891 A | 7/1987 | de Macario et al. | 356/244 |
| 4,918,611 A | 4/1990 | Shyu et al. | 364/474.08 |
| 5,031,099 A | 7/1991 | Kettler | 364/999.999 |
| 5,568,384 A | 10/1996 | Robb et al. | 364/419.13 |

(Continued)

FOREIGN PATENT DOCUMENTS

DE 82 20 792 U1 10/1982

(Continued)

OTHER PUBLICATIONS

Bio Spectrum vol. 10, No. 3 (2004), New Application Fields of Laser Microdissection in Research and Practice, Renate Burgemeister pp. 332-334.

(Continued)

*Primary Examiner*—Aaron W Carter
(74) *Attorney, Agent, or Firm*—Fitzpatrick, Cella, Harper & Scinto

(57) ABSTRACT

The present invention relates to processing a material. The material lies on a carrier and is cut by irradiation with a laser beam, or an object of the material is catapulted from the carrier to a collection device by means of the laser beam. An image of the material on the carrier is generated. The image is evaluated automatically in order to identify structures in it. A region of the image is automatically selected on the basis of the identified structures. The selected region is then used for automatically cutting the material and/or catapulting the object, or serves as a working region in which the material is cut or from which the object is catapulted. Parallel sections through the material may in particular be employed.

45 Claims, 8 Drawing Sheets

U.S. PATENT DOCUMENTS

| | | | |
|---|---|---|---|
| 5,790,692 A | 8/1998 | Price et al. | 382/133 |
| 6,118,582 A | 9/2000 | Del Buono | 359/398 |
| 6,381,353 B1 | 4/2002 | Weiss | 382/133 |
| 6,528,279 B2 | 3/2003 | Yokota et al. | 435/40.5 |
| 6,594,586 B1 | 7/2003 | Song et al. | 702/19 |
| 6,690,470 B1* | 2/2004 | Baer et al. | 356/417 |
| 6,713,264 B2 | 3/2004 | Luttermann et al. | 435/70.1 |
| 6,867,038 B2 | 3/2005 | Liotta et al. | 435/29 |
| 6,991,714 B1 | 1/2006 | Gauss et al. | 204/462 |
| 2001/0033414 A1 | 10/2001 | Yahiro | 359/383 |
| 2002/0048747 A1 | 4/2002 | Ganser | 435/4 |
| 2002/0081014 A1 | 6/2002 | Ravkin | 382/134 |
| 2002/0090122 A1* | 7/2002 | Baer et al. | 382/128 |
| 2002/0101654 A1 | 8/2002 | Pfeifer | 359/391 |
| 2003/0203461 A1 | 10/2003 | Bova | 435/173.7 |
| 2004/0023320 A1 | 2/2004 | Steiner et al. | 435/40.5 |
| 2004/0026630 A1 | 2/2004 | Mohun et al. | 250/458.1 |
| 2004/0071320 A1 | 4/2004 | Pfister | 382/131 |
| 2004/0093166 A1* | 5/2004 | Kil | 702/19 |
| 2005/0163659 A1 | 7/2005 | Duveneck et al. | 422/61 |
| 2007/0153369 A1 | 7/2007 | Schütze et al. | 359/391 |
| 2008/0285795 A1* | 11/2008 | Maddison et al. | 382/100 |

FOREIGN PATENT DOCUMENTS

| | | |
|---|---|---|
| DE | 38 36 716 A1 | 5/1990 |
| DE | 42 11 904 A1 | 11/1992 |
| DE | 196 16 216 A1 | 10/1997 |
| DE | 196 29 141 A1 | 4/1998 |
| DE | 198 04 800 C2 | 8/1999 |
| DE | 198 15 400 A1 | 10/1999 |
| DE | 695 10 925 T2 | 2/2000 |
| DE | 100 37 203 C1 | 4/2002 |
| DE | 102 29 880 A1 | 1/2004 |
| DE | 10 2004 051 508 | 6/2005 |
| DE | 10 2004 023 262.8 | 12/2005 |
| EP | 0 014 857 A1 | 9/1980 |
| EP | 0 100 475 | 2/1984 |
| WO | WO 90/10273 A1 | 9/1990 |
| WO | WO 96/09594 A1 | 3/1996 |
| WO | WO 97/29355 A1 | 8/1997 |
| WO | WO 01/33190 A2 | 5/2001 |
| WO | WO 01/73398 A1 | 10/2001 |
| WO | WO/02/10834 | 2/2002 |
| WO | WO 02/48949 A1 | 6/2002 |
| WO | WO 02/084368 A1 | 10/2002 |
| WO | WO 02/093450 A1 | 11/2002 |
| WO | WO 03/036266 A1 | 5/2003 |
| WO | WO 03/090169 A1 | 10/2003 |
| WO | WO 03/096018 A2 | 11/2003 |
| WO | WO 03/105675 A2 | 12/2003 |
| WO | WO 2004/025569 A2 | 3/2004 |
| WO | WO 2005/040762 A | 5/2005 |
| WO | WO 2005/114135 | 12/2005 |

OTHER PUBLICATIONS

Brochure of P.A.L.M. (2003): Palm MicroBeam IP-MS + Metafax P.

* cited by examiner

METHOD FOR PROCESSING A MATERIAL BY MEANS OF A LASER IRRADIATION AND CONTROL SYSTEM This application is a continuation of International Application PCT/EP2005/003344, with an international filing date of Mar. 30, 2005, which claims the benefit of German Application No. 10 2004 023 262.8, filed May 11, 2004, the priorities of both of which are hereby claimed. The International Application is incorporated by reference herein in its entirety, and was published in German as International Publication No. WO 2005/114135 on Dec. 1, 2005.

FIELD

The present invention relates to a method for processing a biological or nonbiological material, as well as to a control system for a device for processing a biological or nonbiological material. In particular, the present invention relates to a method for the simplified processing, separation and/or extraction of microscopically small biological and/or nonbiological objects from a biological or nonbiological material, and to a control system for a device configured therefor.

BACKGROUND

For a multiplicity of biological studies, it is necessary to isolate individual cells or structures from a cell ensemble, for instance tissue or a histological tissue preparation. This may for example be done with mechanical microtools, for example microcapillaries or microneedles. Such a procedure is laborious, however, and there is a contamination risk for the objects being isolated. Furthermore, such a method is scarcely automatable.

WO 97/29355 A in the name of the Applicant has therefore proposed a novel method for sorting and extracting individual biological objects, which are arranged on a planar carrier. In particular, it proposes separating a selected biological object from the surrounding other biological material by a laser beam, so as to prepare the selected biological object to be free from its surroundings. The biological object prepared to be free in this way is subsequently transferred in a catapult fashion from the carrier to a collection device with the aid of a laser shot, this collection device being for example a collection substrate. For example, a polymer film may be used as the carrier of the biological material.

A biological object to be separated from a biological material applied on the carrier is thus first selected, then cut out from the biological material and subsequently catapulted to the collection device by a laser-induced transport process. In the scope of the present application, "biological objects" are above all intended to mean living or fixed biological cells or cell components which are part of a liquid or solid biological substance, for example cell tissue, a smear, a cell culture or the like.

With the aid of the method described above particular objects can be deliberately detached or sorted from a biological material. The biological objects may be applied next to one another on a fixed planar carrier, and the process of extraction or sorting can be carried out within a short time and contactlessly. The survivability and the morphology of the biological objects are preserved, i.e. the biological objects are not damaged or harmed by the separation process and the laser-induced transport process.

The method described above, however, is to be carried out manually and is therefore relatively elaborate. High precision is furthermore necessary, since a biological object to be separated must be positioned precisely with respect to the laser beam in order to achieve reliable cutting and subsequent catapulting by a laser pulse or laser shot. Furthermore, in general similar cutting processes or catapulting processes must be carried out repeatedly with high accuracy.

For this reason, WO 01/73398 A in the name of the Applicant proposes to carry out the cutting and/or catapulting of the object with computer assistance. It proposes that a laser light source, which generates the laser beam used for the cutting and/or catapulting, should be controlled automatically and the relative movement between the laser beam and the carrier comprising the biological object, which is required for the cutting and/or catapulting, should be induced and controlled automatically. In particular, a plurality of cutting and/or catapulting processes can be carried out successively with computer assistance, i.e. automatically. This can ensure a uniform high precision for each individual cutting/catapulting process.

According to this method, the objects to be cut out or catapulted are selected by means of a user interface of a computer system. To this end a video image of the biological or nonbiological material is generated and overlaid with the user interface of the computer system. Manual selection of a multiplicity of objects by the user, however, entails considerable time expenditure. The manual selection of objects furthermore involves a risk that the selection will not be made according to objective criteria.

SUMMARY

It is therefore an object of the present invention to provide a simplified and more effective method for processing a biological or nonbiological material as well as a control system for a corresponding device, so as to eliminate the problems described above and in particular ensure less work for the user and reliable separation of objects from the material according to objective criteria. This object is achieved according to the invention by a method and/or a control system. The invention furthermore relates to a device for processing a material with a laser beam, particularly in the form of a laser microscope system or a laser microdissection system, and to a computer-readable computer program product having a program code for carrying out the method according to the invention, which may in particular be a commercially available data medium (hard disk, CD-ROM, DVD, diskette etc.) as well as an electronically readable storage medium (for example a memory integrated into a computer system). The dependent claims define respectively preferred and advantageous embodiments of the invention.

The present invention will be described below primarily with reference to cutting and/or transferring biological objects. The invention is nevertheless likewise applicable for nonbiological objects (nonliving substance), which may for example be microscopically small objects of glass, silica, plastic or artificially produced vesicles in a biological material. The present invention is likewise applicable to nonbiological materials, for example polymer materials or the like, from which microscopically small objects are to be extracted.

According to the invention, cutting of the material and/or transferring of an object is carried out by means of a laser beam. In this process, the material is located on a carrier, e.g. a microscope table, and after the catapulting process the object is collected in a collection device. As, due to the irradiation with the laser beam, the transferring occurs in an impulse-like fashion or a catapult-like fashion, in the following it will be referred to a catapulting of the object respectively irradiated with the laser beam.

A basic idea of the present invention is for structures to be identified or classified in an image of the material, which structures are then used to automatically select a region of the material where the material is cut and/or the object is catapulted. The automatic identification of structures and selection of the region are preferably performed in a flexible object-oriented fashion on the basis of the relationships of the structures to one another. This means that structures can firstly be identified on the basis of contrast information in the image, for example colour or brightness contrasts, but in addition a hierarchy of structures can be defined so that superordinate structures are defined which comprise subordinate structures. In this case, it is possible to identify the structures on the basis of the respective neighbouring, superordinate or subordinate structures. The selected region may in particular be such an identified structure, i.e. the region is selected so that essentially only the identified structure is contained in it.

Compared with a conventional evaluation of images, which is based merely on contrast information, this flexible object-oriented identification of structures offers the advantage of setting up a structure hierarchy which allows much more effective recognition of structures. Rule sets can be defined for the identification so that the identification of structures, and region selection based on this, is performed according to precisely defined objective criteria. The identification and selection process can be configured flexibly with the aid of the rule sets so that, for example, identification is also possible merely on the basis of contrast information, for example colour or brightness contrasts.

The invention provides a method, according to which an image of at least a part of the material on the carrier is generated by imaging means. The image is evaluated automatically, in order to identify predetermined structures in the image. These structures may, for example, be cell nuclei, cell membranes, whole cells or cell groups. A region of the image is selected automatically on the basis of the identified structures. Characteristic geometrical quantities of the selected region are subsequently determined, and a control signal for automatically cutting the material and/or catapulting the object is generated on the basis of the characteristic geometrical quantities.

By the procedure according to the invention an automated selection of a region of the image is performed, characteristic geometrical quantities of which are then determined. These characteristic geometrical quantities preferably comprise firstly a position of the selected region on the carrier or a circumferential line of the selected region, which is defined with respect to the carrier. Further characteristic quantities, which preferably comprise a section curve or a target point, can then be determined on the basis of the position or circumferential line.

Control signals for automatically cutting the material and/or catapulting the object are generated on the basis of the characteristic geometrical quantities.

Said steps can be carried out by correspondingly configured image processing means and data processing means, for example in a computer system. The user's workload for cutting the material and/or catapulting the object from the material is thus significantly reduced, since no manual selection of regions or objects is now necessary. The separation of objects from the material can furthermore be performed according to objective criteria which, for example, may be defined abstractly in a rule set.

When generating the control signal for automatically cutting the material, the section curve is preferably determined on the basis of the circumferential line of the selected region. This is done particularly in that the section curve is separated from the circumferential line of the selected region by at least a predetermined distance and encloses the circumferential line of the selected region. This ensures that the laser beam does not directly strike the selected region of the material during the cutting process, and damage to the selected region can therefore be avoided. It may furthermore be advantageous in particular to select this predetermined distance as a function of the identified structures so that, for example, a larger distance can be automatically selected for structures classified as particularly sensitive or structures with an inaccurately defined edge region.

The generation of control signals for automatically cutting the material and/or catapulting the object may furthermore comprise automatic determination of the control parameters of a laser light source for generating the laser beam. This further simplifies the entire process for the user since manual adjustment of control parameters, for example a laser power or a pulse duration, is not necessary. It is furthermore possible to adapt the control parameters automatically to structures respectively identified in the environment of the selected region or inside the selected region.

In the present invention, the cutting is performed by moving the laser beam in the activated state along the section curve relative to the material. This creates a section line in the material which may in particular fully enclose an object in the material, which is subsequently to be catapulted. It is nevertheless also possible not to fully close the section line, so that the object to be catapulted is fixed with respect to the material until the catapulting process. The relative movement between the material on the carrier and the laser beam is preferably induced by an adjustment device, which is driven and adjusted by an adjustment control signal. The adjustment control signal is generated on the basis of the calculated section curve, so that the laser beam is moved along the section curve for the automatic cutting.

The characteristic geometrical quantities of the selected region which are calculated according to the method according to the invention may furthermore comprise the target point, the control signal of the adjustment device being generated on the basis of this target point so that the laser beam is aimed at the target point for the automatic catapulting, and the object is catapulted from the carrier to the collection device when the laser beam is subsequently activated. This target point may for example be defined by a geometrical midpoint of the selected region or else lie on the calculated section curve, in which case the cutting of the material is performed so that the resulting section line is not closed at the position of the target point. The target point for the catapulting process can accordingly be determined automatically, so that precise selection of the target point is possible and a high reproducibility and reliability of the catapulting process is achieved.

In the present invention, the material is typically arranged on an object carrier means. In conjunction with the automatic selection of regions of the image, high effectiveness together with less work for the user are ensured in the separation process.

It is particularly advantageous for essentially the entire object carrier means to be imaged when generating the image. In this way, all the regions of the material which lie on the object carrier means can be included for the automatic evaluation of the image. The object carrier means may, for example, be a glass object carrier on which a histological tissue section is arranged.

The imaging means are preferably formed by a microscope, which comprises an objective arranged above or below the object carrier means. Owing to the elongate rectangular shape which is conventional for glass object carriers and the typical magnification ranges of microscope objectives, it is then generally not possible for the entire glass object carrier to be imaged through the microscope objective. For this reason, according to the present invention the image may be generated by combining a plurality of sub-images which are respectively obtained by relative movements of the carrier, with the object carrier means lying on it, with respect to a receiving means or objective of the imaging means. In this way it is possible to image a large region of the object carrier means, and at the same time achieve a high resolution of the image.

The image or the sub-images are preferably obtained in that a suitable camera, for example a CCD camera, is coupled to optics of the receiving means and the image recorded by the camera is converted into a format suitable for the automatic evaluation. This format may, in particular, be a digital image format suitable for digital image and data processing means.

It is particularly advantageous for the sub-images to be generated in such a way that at least one overlap region between the sub-images is formed when the sub-images are combined to form the image. This means that a particular region of the material or the object carrier means is contained on each of two neighbouring sub-images. This firstly ensures that no image information is lost at the interfaces between the sub-images. In conjunction with the method according to the invention, moreover, it is particularly advantageous for this overlap region between the neighbouring images to be likewise evaluated automatically in order to identify structures corresponding to one another in it, so that the sub-images can be aligned with the aid of these identified structures during the subsequent combination of the sub-images to form the image. In this way the image can be assembled from the sub-images without errors occurring in the image, which may for example be caused by insufficient precision in the relative movement of the carrier with respect to the receiving means of the imaging means.

The method is preferably configured so that a plurality of regions are automatically selected during the automatic evaluation of the image, and the characteristic geometrical quantities of each selected region are stored. The control signals for automatically cutting the material and/or transferring the object are then respectively generated on the basis of the stored characteristic geometrical quantities of the selected regions.

In this way, the entire separation process can be configured so that an evaluation of the image is performed first and then the stored characteristic geometrical quantities are preferably processed successively in the form of a list. In particular, the sequence of the cutting and catapulting processes can thus be configured much more effectively. Overall, it is therefore possible to achieve a much higher speed for the entire procedure.

It is particularly advantageous in this context for manual selection of regions to be possible as well, and for the characteristic geometrical quantities of the automatically selected regions to be stored in the same format as those of the manually selected regions. In this way the components required for a corresponding control system are firstly simplified, or their number is reduced. It is furthermore possible to configure such a control system in a modular fashion, in which case the functions for automatically selecting regions and calculating characteristic geometrical quantities may be provided as an extension of a semiautomatic system in which the cutting and/or catapulting process is performed automatically, i.e. is computer controlled, but the selection of regions or determination of section curves or target points is performed manually.

Further, after the automatic cutting of the material, a further image may furthermore be generated which is in turn automatically evaluated in order to identify a predetermined structure therein in the form of an incomplete section line around the selected region. If such is the case then a section curve is determined, on the basis of which control signals are generated for re-cutting the material automatically so that the incomplete cut is completed. This ensures increased reliability of the cutting process.

The present invention furthermore relates to a method which concerns a case in which the material lies on a carrier and is divided into a plurality of parts. These parts of the material may in particular be essentially parallel sections through the material, which are for example respectively arranged on an object carrier means, for example so-called serial sections. The sections typically have a thickness of a few micrometres.

In this method, an image is generated for each of the parts of the material by imaging. The images are evaluated automatically in order to identify recurring structures in them. These recurring structures may be structures of the material or an artificially induced marking which leads to a recurring structure in each part of the material. It is then possible to specify a particular form of recurring structure, for example caused by the artificial marking, or to determine such a recurring structure by the automatic evaluation without prior commitment to a particular structure. According to the invention, a region of the image is selected for at least a part of the material on the basis of the identified structures. The material is then cut in the selected region and/or the object of the material is catapulted from the selected region.

In this case the automatic selection of the region is not used in the first place to determine characteristic geometrical quantities of the region on the basis of it, which are then used in order to generate control signals for cutting the material and/or catapulting the object. Rather, in this case a region is selected which corresponds to a region in another part of the material or a plurality of regions respectively in other parts of the material. In this way a region can be selected manually or automatically in one part of the material, and a corresponding region in at least one other part of the material can be automatically selected.

Such regions corresponding to one another occur, for example in the case of a plurality of histological sections taken parallel to one another, when a structure of the material extends over a plurality of section planes in a direction perpendicular to the plane of the sections. For studies, it is often desirable to prepare objects from one section and from a corresponding region of a further section. In a conventional method, however, this entails considerable work or even is entirely impossible. This is attributable inter alia to the fact that structures which extend over a plurality of sections usually change from section to section or may entirely vanish. It is furthermore possible for the sections to be displaced, rotated or deformed relative to one another during preparation.

Furthermore, staining is sometimes carried out on the sections in order to emphasise particular structures in them. This makes it possible to select a region of interest in such a section. Owing to the staining, however, it is sometimes not appropriate to take objects from this section.

With the method according to the invention, it is possible to make a corresponding region findable in another section which, for example, is not stained. This region is then available as a working region for cutting the material and/or catapulting an object of the material.

Preferably, as described above, regions are in turn automatically selected in this working region, characteristic geometrical quantities are calculated and control signals are generated for automatically cutting the material and/or catapulting the object on the basis of the characteristic geometrical quantities. It is also possible to automatically select the entire working region and subsequently perform a corresponding cutting and catapulting process. It is nevertheless also possible to manually select regions inside the working region, or manually specify section curves and/or target positions.

For identification of the recurring structures of the parts of the material, which is preferably performed in the object-oriented way described above, a rule set is preferably specified according to the type of recurring structures. In general the rule sets differ according to whether, for example, particular predetermined structures are to be identified or recurring structures are to be identified in different images. It is therefore advantageous to specify rule sets respectively for different tasks, and to select a corresponding rule set for the identification process in question.

The aforementioned artificial generation of recurring structures in parallel sections may be carried out according to the invention in that before generating the parallel sections, the material is provided with marking which leads to a recurring structure in each of the sections. This can subsequently be identified and used for defining the working region. Such marking is preferably carried out using three hole regions, which are created in the material in a direction essentially extending perpendicularly to the planes of the parallel sections. Identification of the three hole regions is reliably possible with the automatic evaluation according to the invention. Such hole regions can furthermore be recognised and marked by the user with a tolerable workload.

It is particularly advantageous for the recurring structures to define at least three positions in the respective section. Reference points, which are defined with respect to the carrier, can then be determined with the aid of these positions. When these reference points are determined for two of these sections, a transformation matrix can therefore be determined from these positions, which makes it possible for position specifications of the one section and position specifications of the other section to be converted into one another.

The transformation matrix preferably takes into account displacements, rotations or deformations of the sections relative to one another. Position specifications of various sections or their images can be reliably converted into one another by the transformation matrix, so that a corresponding region of another section can be made findable in a controlled way.

When the reference points are defined by the hole regions they may also be manually selected with a tolerable workload, so that automatic evaluation of the images is sometimes unnecessary for determining the transformation matrix.

The invention furthermore relates to a control system for a device for processing a material by laser irradiation. To this end, the device comprises in particular a carrier on which the material lies. The device furthermore comprises a laser light source for generating a laser beam in order, by irradiation with the laser beam, to cut the material and/or catapult an object of the material to a collection device. The device also comprises imaging means for generating at least one image of at least a part of the material. The control system according to the invention comprises control means for automatically controlling the laser light source and for automatically controlling adjustment means to induce a relative movement between the laser beam and the material. The control system furthermore comprises image processing means for automatically evaluating the image or plurality of images in order to identify structures therein, and data processing means which are configured in order to select a region of the at least one image automatically on the basis of the identified structures.

The control system according to the invention is therefore capable of evaluating images automatically in order to identify structures in them, and of automatically selecting a region of the image on the basis of this. This region may on the one hand be used as a working region in order to select further structures in it, or characteristic geometrical quantities of the selected region may be determined. It is in particular advantageous for the control means to be configured in order to generate control signals for automatically cutting the material and/or catapulting the object on the basis of the characteristic geometrical quantities of the selected region of the image. The control system according to the invention is therefore suitable in particular for carrying out one of the methods according to the invention with a device of the type described above.

The invention furthermore relates to a device for processing a material, which has a control system according to the invention and may in particular be configured for carrying out one of the methods according to the invention.

The advantages of the invention are that it allows for finding objects or regions of material much more rapidly. The selection of objects or regions is furthermore carried out according to objective criteria, i.e. according to particular rules, which avoids subjective influences due to manual selection by the user and increases the reproducibility of the processing. It is furthermore possible to define various rule sets which are adapted to make particular structures findable, in which case it is merely necessary to select a corresponding rule set for a particular task, for example separating cells of a particular tissue type. Furthermore, it makes it easier to find regions corresponding to one another in the case of serial sections, which for example provides the opportunity to emphasise structures by staining in one or more sections but to take objects from a corresponding region of another section, which is not stained and is therefore also not chemically modified or contaminated.

BRIEF DESCRIPTION OF THE DRAWINGS

The invention will be explained below with reference to the appended drawings with the aid of preferred exemplary embodiments.

DETAILED DESCRIPTION

Figure 1:
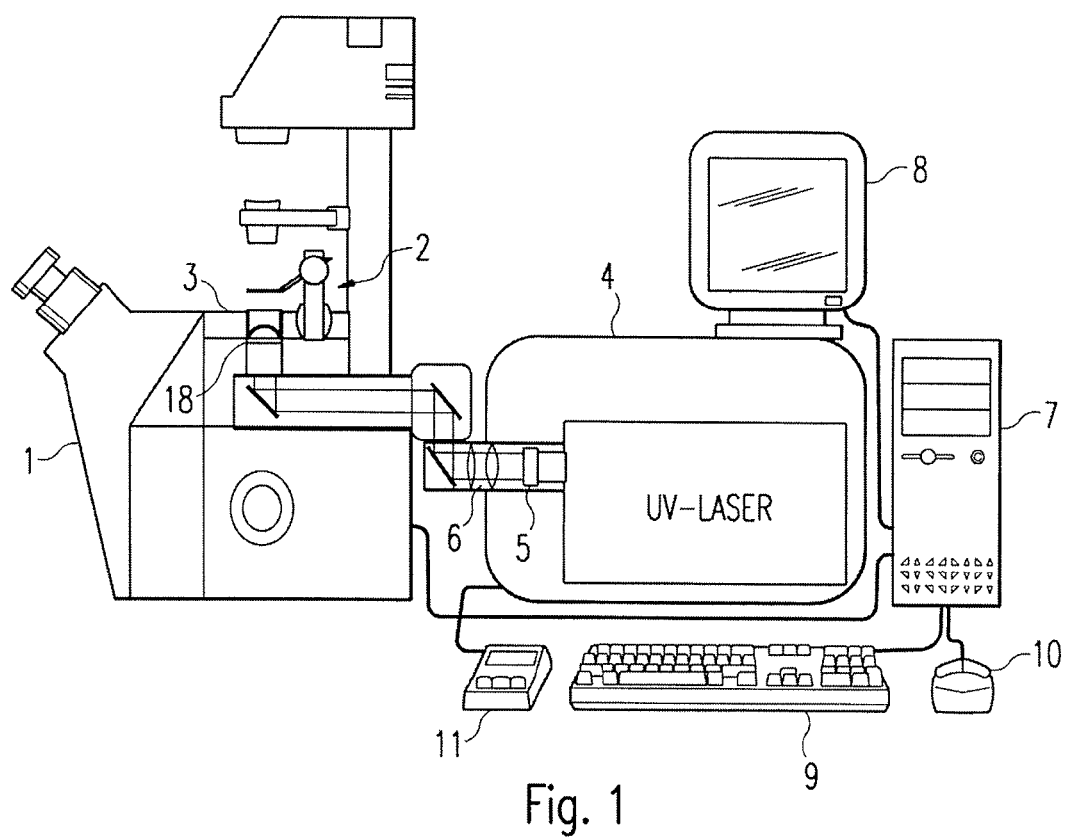
FIG. 1 shows a schematic structure of a device for carrying out the present invention.

FIG. 1 represents the structure of a laser microscope system such as may be used for carrying out the present invention. The system is constructed in a modular fashion, and can therefore be adapted individually to various experimental requirements. The laser microscope system represented is in particular an inverse laser microdissection system for separating, i.e. detaching, biological objects such as individual cells or cell components from a biological substance or preparation, although the invention is not of course restricted to this preferred configuration. The invention may, for example, also be applied to erect laser microscope systems or to the processing of nonbiological substances. Likewise—depending on the specific applications—the use of a microscope may optionally be obviated.

The essential component of the system represented in FIG. 1 is a laser device 4, in which a laser light source is fitted for generating a laser beam. Optics 5, 6 are furthermore fitted in the laser device 4, which are used for coupling the laser light into a microscope 1 and for tuning the laser focus in the object plane onto the optical focus of the microscope 1. The present case involves a pulsed UV nitrogen laser, whose wavelength is 300 nm and whose pulse energy is for example 270 microjoules. The pulse duration is 3 ms, while the pulse frequency can be adjusted between 1-30 pulses per second.

The nitrogen laser emits a laser beam with a fixed laser energy. For precise laser micromanipulation and laser microdissection, accurate adjustability of the laser energy is required. For this reason, a quartz filter 5 is arranged perpendicularly to the laser beam path. This quartz filter is rotated by a DC motor which can be controlled via a potentiometer knob (not shown), so as to adjust the laser energy accordingly.

Besides adjusting the laser energy, it is also possible to adjust the laser focus independently of the microscope focus i.e. the focal point of the laser can be displaced in the z direction relative to the object plane of the microscope 1. To this end a stepper motor is provided, which moves the lenses 6 shown in FIG. 1. The focusing, or the stepper motor, can in turn be controlled by a potentiometer knob.

The laser beam is coupled into the microscope 1 via a plurality of coated beam splitters and deflected towards an objective 18. The diameter of the laser beam arriving on the object plane depends crucially on the numerical aperture of the objective 18. An objective with a relatively high numerical aperture permits laser beam diameters of less than 1 μm. It is furthermore important for the objective 18 respectively used to have a high transmissivity for the laser wavelength, in order to minimise energy losses.

The laser beam emitted via the objective 18 finally impinges on a motorised and computer-controlled microscope or carrier stage 3, on which an object carrier means is arranged with a biological material to be processed.

Above the carrier stage 3, there is a likewise motorised and computer-controlled collection device 2. The microscope stage 3 and the collection device 2 allow exact positioning with a precision in the nanometre range, as well as automatic conduct of the micromanipulation procedures.

The motorised microscope stage 3 can be moved along two linear axes (x and y direction). To this end, two hybrid stepper motors with three steps per 360° revolution are provided. The minimum step size is 20 nm, so that object carrier means lying on the microscope stage 3 can be positioned with very high accuracy.

The collection device 2 is used to collect biological objects catapulted away from the microscope stage 3, or the object carrier means. The motorised collection device 2 can likewise be moved in both the x and y directions. Mobility in the z direction is also provided. For this purpose three stepper motors are provided, which have the same precision as the stepper motors provided for the microscope stage 3.

The microscope 1 may be a microscope configured in any way. In particular, it is conceivable to use both an inverse and an erect microscope or a laser microscope. The microscope 1 is fitted with a camera, particularly a CCD (charge coupled device) camera, which records the region of the microscope stage intended to receive the object carrier means. The camera may record the image via the microscope objective 18, or it may have its own optics for imaging object carrier means arranged on the microscope stage 3. The video signal of this camera is fed to a computer system 7 which, for example, may be a commercially available personal computer.

The video signal is processed in the computer system 7, for example with a frame grabber card, and is converted to an image in a digital format which is suitable for further processing in the computer system 7 or in a further computer system connected to it. It is possible to represent the images recorded by the camera in real time on a display screen 8 of the computer system 7. It is furthermore possible for individual images recorded in this way to be stored in a storage medium of the computer system 7 or transmitted via a network to a further computer system.

The computer system 7 furthermore has the function of a control system for the material processing device. To this end the computer system 7 has a corresponding interface card that generates control signals, via which automatic driving of the laser device 4, the microscope 1, the collection device 2 and the microscope stage 3 is possible. Input means which are conventional for computer systems, for example a keyboard 9 or a computer mouse 10, are provided in order to set or select these functions. The laser device 4 is furthermore assigned a foot switch 11, which can be actuated in order to manually activate the laser.

A method for processing a biological or nonbiological material, which is to be carried out with the system described above, will be explained in more detail below. In general these method steps are processes carried out automatically, which are conducted or controlled by the computer system 7. Optionally, however, processes are also initiated or carried out manually.

Figure 2:
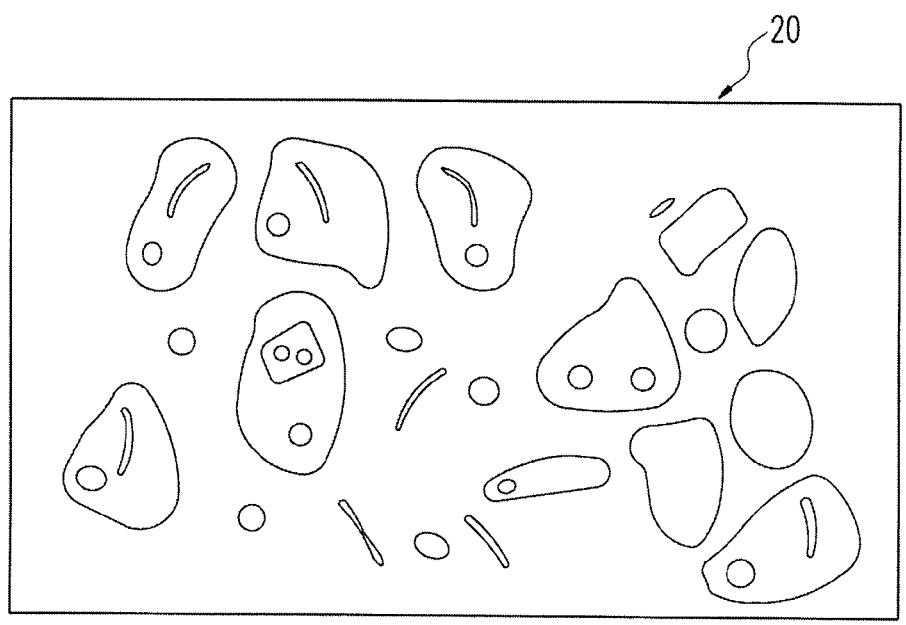
FIG. 2 shows an image of a biological material by way of example.

An image of the biological material on the microscope stage 3 is first generated with the camera via the objective 8 of the microscope 1. An example of such an image is represented in FIG. 2, where it is denoted by the reference numeral 20. In order to generate the image, the video signal of the camera is converted into a pixel-based digital image format in the computer system 7.

The image 20 of the material as represented by way of example in FIG. 2 shows miscellaneous structures, which are manifested in contrast differences of the image 20. In particular, it can be seen that the structures may have various shapes and sizes. It can furthermore be seen that some of these structures are contained inside other structures, or that particular structures neighbour one another.

Figure 3:
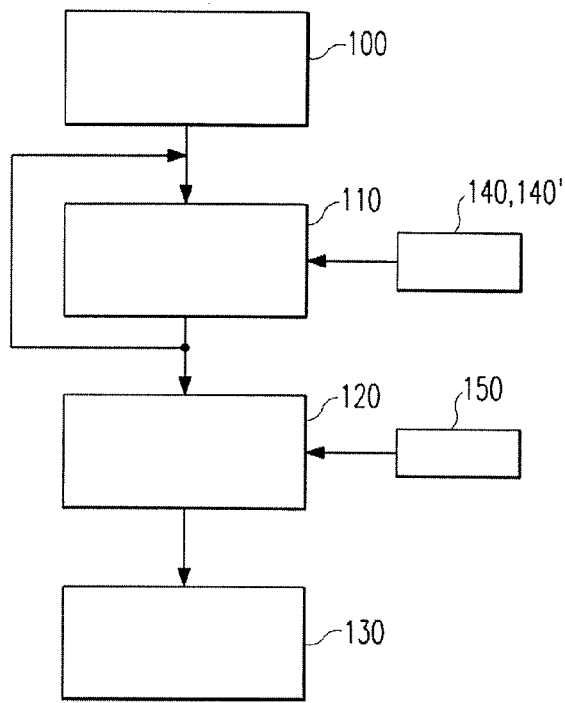
FIG. 3 shows a flow chart for a method according to one exemplary embodiment of the invention.
Figure 7:
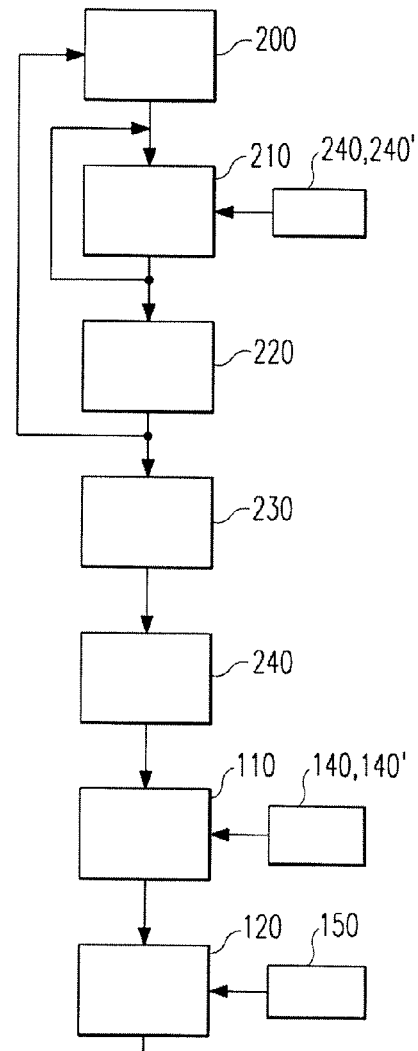
FIG. 7 shows a flow chart for a method according to a further exemplary embodiment of the invention.

FIG. 3 represents a flow chart for the method. In imaging step 100, the image of at least a part of the material on the microscope stage 3 is generated by means of the camera via the objective 18 of the microscope. The image is converted in the computer system 7 into a format suitable for the further processing.

In order to automatically evaluate the image in step 110, it is sent to an image processing unit in the format suitable therefor. The image processing unit is embodied as a function module inside the computer system 7 by corresponding software. Predetermined structures in the image are identified by the evaluation. They may be structures as represented in FIG. 2. To this end a corresponding rule set 140, which contains predetermined features that the structures to be identified comprise, is fed to the image processing unit. These features may in particular contain colour contrasts or brightness contrasts, or relationships of the structures to one another. Such a rule may for instance specify that a particular structure contains a further structure, in order to identify the structure. A rule that particular structures neighbour one another may furthermore be provided.

A region of the image 20 is selected on the basis of the identified structures, whereupon the evaluation step may be repeated in order to select further regions. This may be done on the basis of the same rule set 140, although it is also possible to use another rule set 140'. The rule sets 140, 140' may be selected by the user from a group of predetermined rule sets, or may be defined directly by the user.

After selecting at least one region of the image, characteristic geometrical quantities of the selected region are determined in a calculation step 120. These characteristic geometrical quantities comprise firstly a position of the selected region on the microscope stage 3 as well as a circumferential line of the selected region, which is defined with respect to the microscope stage 3. The circumferential line may be defined as a polygon contour or a line contour without sharp corners, for example as a spline. In this way, with a small number of points, it is possible to define a circumferential line of the selected region which is closely aligned with the structures lying in it. In addition, for example, a surface content or an average brightness of the selected region may be determined. If a multiplicity of regions are selected automatically, for example, these quantities may be used for statistical purposes.

A section curve and a target point are determined as further characteristic geometrical quantities of the selected region for further use in an automatic cutting or catapulting process. The section curve is established so that the circumferential line of the selected region is contained in it, the section curve being at least at a predetermined distance from the circumferential line of the selected region. This predetermined distance ensures that structures lying in the selected region are not damaged when cutting along the section curve. This predetermined distance may be rigidly predetermined by the user, or adapted dynamically on the basis of the identified structures, for example the brightness determined for the selected region. An increased distance may be selected for structures classified as particularly sensitive. The same is expedient for structures which have only an inaccurately defined edge region.

A target position, at which the laser beam is aimed for catapulting the object, is furthermore determined. This target position may be determined by the geometrical midpoint of the selected region, i.e. a two-dimensional centroid. This ensures precise alignment of the catapulting process. Alternatively, when the intention is not to cut fully around the selected region, this target point may be placed between the endpoints of the incomplete section line in the region. This ensures that the object to be catapulted is fixed with respect to the biological material until the catapulting process.

The characteristic geometrical quantities, which are determined automatically in the calculation step 120, are sent to control means in the form of a control unit to generate control signals for automatically cutting the biological material and/or catapulting the object. In the subsequent control signal generation step 130, control signals for automatically cutting the biological material and/or catapulting the object are generated on the basis of the characteristic geometrical quantities, particularly on the basis of the section curve and/or the target point. They contain control signals and control parameters for the laser device 4 and for the adjustable microscope stage 3. Control signals are furthermore generated for the collection device 2, in order to collect the catapulted object at a particular position of the collection device 2. For the cutting process, control signals for the microscope stage 3 are generated which induce a relative movement of the object carrier means, arranged with the biological material on the microscope stage 3, with respect to the laser beam. The relative movement between the biological material and the laser beam is controlled so that the laser beam moves along the previously determined section curve. At the same time, the laser beam is activated so as to cause the desired cutting of the material around the selected region. Corresponding control signals are likewise generated for activating and adjusting the laser device 4. To catapult the object, an adjustment signal is generated for the microscope stage 3, the effect of which is that the laser beam is aimed at the previously determined target point. A corresponding control signal for the laser device 4 thereupon causes a laser pulse or laser shot, which catapults the object or selected region into the collection device 2.

According to the method, a plurality of regions may be selected, for which the characteristic geometrical quantities are respectively determined. The characteristic geometrical quantities are stored for the various regions, and then processed in the form of a list in order to generate the control signals for the microscope stage 3 and the laser device 4.

It is furthermore possible to select objects manually with the aid of the input means 9, 10 of the computer system 7, in which case corresponding characteristic quantities 150 are added to the list and subsequently processed in the control signal generation step 130 together with the characteristic geometrical quantities of the automatically selected regions. The manual selection of regions is preferably performed in that the user places the desired section curve around the region, or marks the desired target point, on the display screen 8 on which the image 20 or a part of the image 20 is represented. The calculated section curves and the section curves manually generated in this way, as well as the target points associated with them, are stored in a common format together with further parameters, for example control parameters of the laser device 4. In the control signal generation step 130, there is therefore no discrimination between the automatically selected and manually selected regions.

It is optionally possible for a further image to be generated after the cutting process, which is then evaluated in order to identify a section line which may sometimes be incomplete.

For the case of an incomplete section line, the corresponding region is selected and a section curve is calculated. Control signals for a new cutting process are then generated on the basis of the section curve.

Figure 4A:
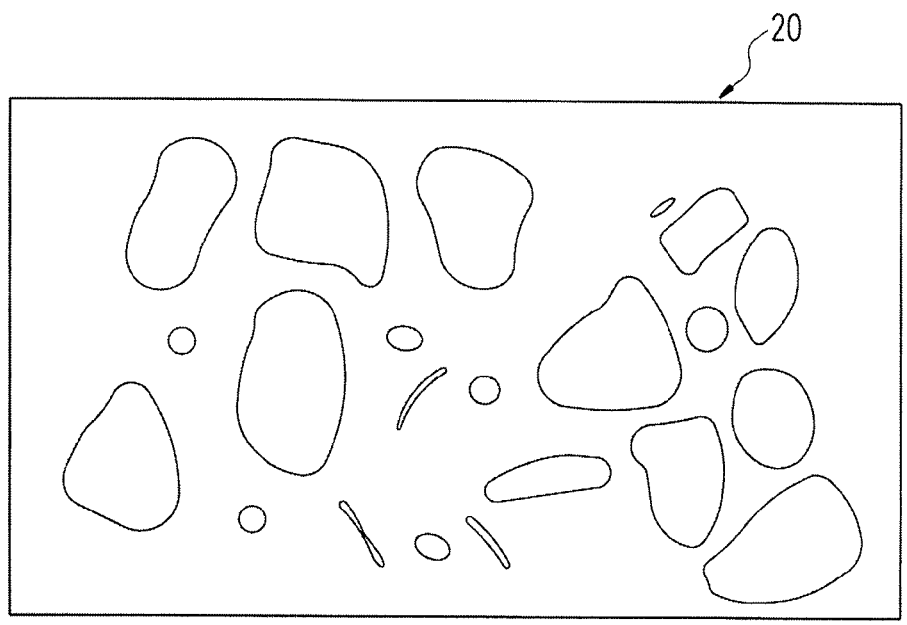
FIGS. 4A and 4B show the image of FIG. 2, respectively identified structures of different hierarchy levels being represented, FIGS. 4C and 4D respectively show the image of FIG. 2, a region or a plurality of regions being selected inside the image and characteristic geometrical quantities determined therefor being represented, FIGS. 5A and 5B respectively show a complete image of an object carrier, the image being composed of sub-images.
Figure 4B:
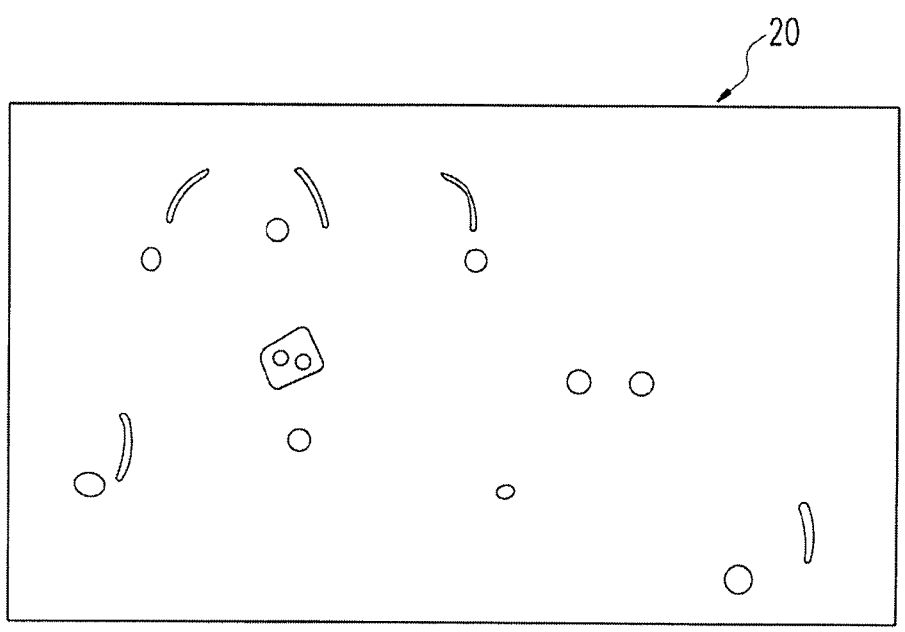

The automatic evaluation to identify predetermined structures will be explained below with the aid of an example. To this end FIGS. 4A and 4B represent structures of the image 20 of FIG. 2, which belong to different hierarchy levels. FIG. 4A represents structures of a superordinate hierarchy level. FIG. 4B represents structures which belong to a subordinate hierarchy level, i.e. they are contained in the structures of FIG. 4A.

The rule set used firstly provides for identifying the structures shown with the aid of contrast information of the image, i.e. assigning them to particular classes. Merely the structures identified in this way, however, are not sufficient in this example in order to select on their basis one or more regions of the image 20 with the desired accuracy. To this end, the relationships of the structures of different hierarchy levels are used according to this rule set. An additional criterion also employed in this case is whether a structure is "elongate" or "round".

Figure 4C:
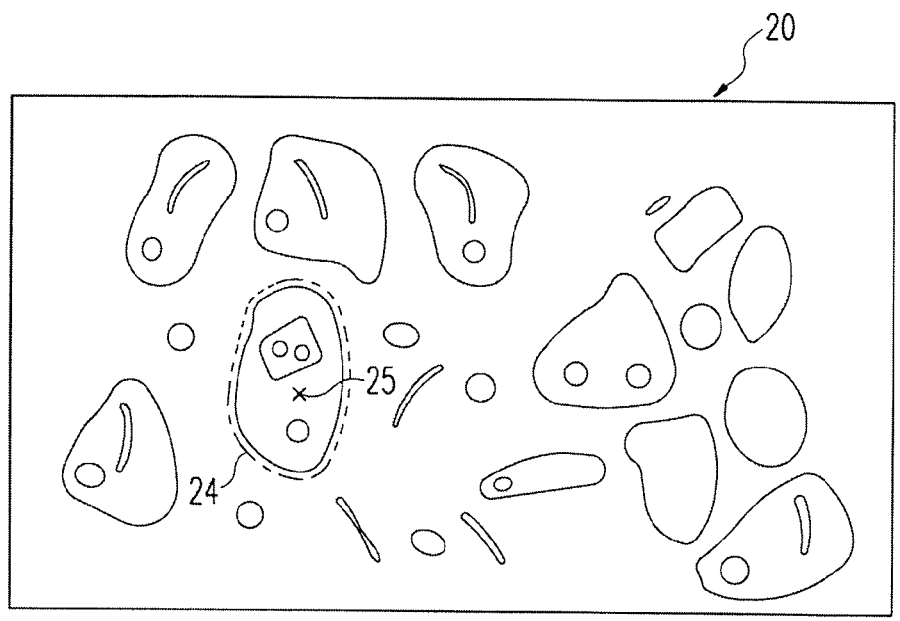

FIG. 4C shows an example of the image 20, in which the rule set defines that a region which contains a structure should be selected, this structure in turn containing two further structures in a subordinate hierarchy level, one of which is "round" and the other in turn contains two structures in a hierarchy level lying further below. For the regions selected on the basis of this rule set, the section curve 24 determined in the calculation step 120 and the target point 25 are represented.

Figure 4D:
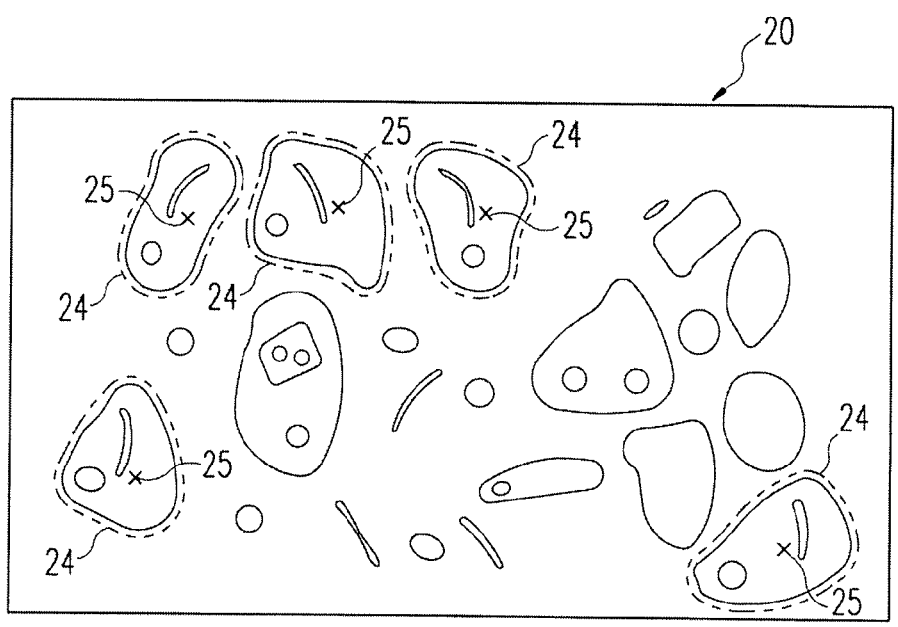

FIG. 4D shows a further example of the automatic selection of regions, another rule set being used which stipulates that the region to be selected contains a structure that contains two structures in a subordinate hierarchy level, one of which is classified as "round" and the other as "elongate". In this case a plurality of regions would be selected automatically.

The above example is merely intended to illustrate the basic principles of the preferred evaluation, which resorts to information from different hierarchy levels. Optionally, however, structures of a single hierarchy level may even be sufficient in order to select a region. This could apply, for example, when the region to be selected has a particularly high brightness contrast or colour contrast with respect to its environment. For particularly prominent shapes, moreover, conventional pattern recognition may be employed.

Figure 5A:
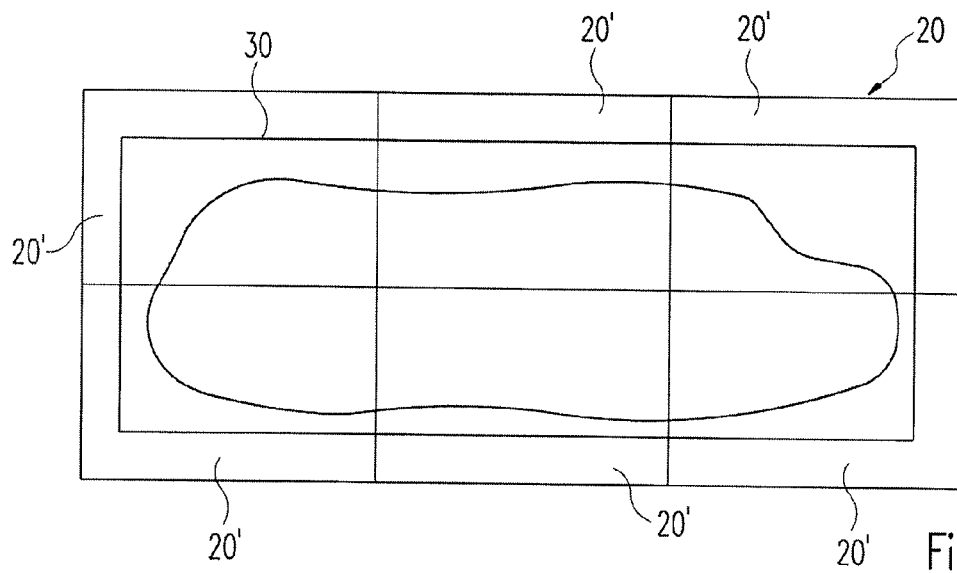
Figure 5B:
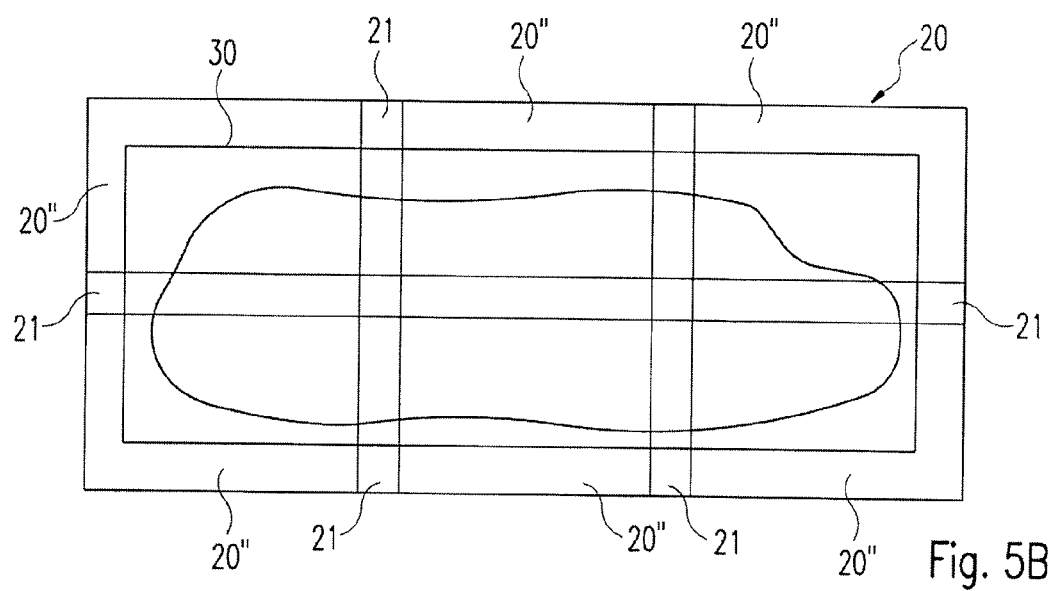

FIGS. 5A and 5B respectively show an image, wherein it can be seen that the image 20 fully represents an object carrier means 30 with a biological material lying on it. To this end, the image 20 is assembled from a plurality of sub-images 20' and 20", respectively. In FIG. 5A, the sub-images 20' are joined flush with one another. Each of the sub-images 20' is generated by generating a video signal by means of the camera of the microscope 1 via the objective of the microscope 1. Each of the sub-images is assigned a special position of the microscope stage 3, with the object carrier 30 lying on it, with respect to the objective 18 so that the represented imaging region for the sub-images 20' is obtained with the selected magnification of the optics. The different positions of the object carrier 30 with respect to the objective 18 are obtained by displacing the microscope stage 30 with respect to the objective 18. The position of the object carrier means 30 with respect to the objective 18 can be adjusted accurately owing to the high precision of the microscope stage 3, so that it is possible to join the sub-images 20' directly to one another. This is in turn done by the image processing means of the computer system 7.

FIG. 5B shows an alternative possibility for combining the sub-images 20". In this case, the imaging regions of the sub-images 20" are selected so that overlap regions 21 are formed between neighbouring sub-images 20". These overlap regions 21 firstly ensure that no image information is lost at the interfaces between the sub-images 20". At the same time, an evaluation of the sub-image may be performed for each of the sub-images 20" in these regions, in order to identify structures corresponding to one another in neighbouring sub-images 20". This is done in the way described above, but with a rule set specially adapted therefor. For this purpose, in the example shown, the edge region of the object carrier 30 could for example be identified. When combining the sub-images 20", they are then aligned by the image processing means so that the structures corresponding to one another, which have been previously identified, are congruent. A high precision can thereby be achieved when combining the images, without additional components or functions having to be provided for this purpose.

Figure 6:
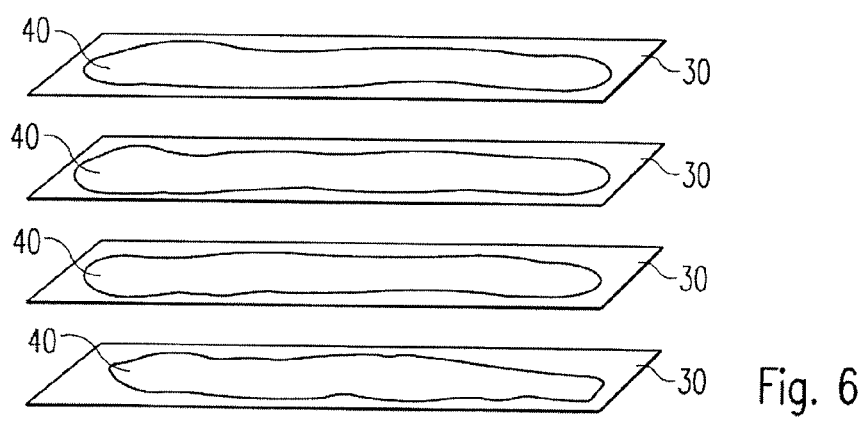
FIG. 6 shows parallel sections through a material, which are respectively arranged on an object carrier means.

An example of a method for processing a biological material will be explained below, which is based on a series of sections through the biological material. These are so-called histological serial sections of a few micrometres thickness, which are taken parallel to one another. An example of such sections 40 is represented in FIG. 6, the sections 40 respectively being arranged on an object carrier means 30. They are in particular serial sections which have been taken at a short distance from one another. Three-dimensional structures, which extend perpendicularly to the section planes in the material, typically lead to a structure which recurs in each of the sections. Such a recurring structure, however, may also be induced artificially by corresponding measures.

In order to be able to prepare objects or substance from such serial sections and then carry out further studies, it may in particular be necessary to find regions assigned or corresponding to one another in the individual sections 40. Such regions corresponding to one another typically originate from a three-dimensional structure of the material, which extends over a plurality of the sections 40 and which can therefore be assigned a corresponding region in each of the sections 40. Manually, however, the identification of such regions corresponding to one another is only possible with considerable work or even sometimes entirely impossible. A problem may furthermore consist in that displacements, rotations or deformations of the sections 40 occur when applying the sections onto the object carrier means 30.

The method therefore proposes that recurring structures in the parts of the biological material, i.e. in the individual sections 40, should be identified by automatically evaluating images. To this end an image 20 is firstly generated in the imaging step 200 for each of the sections 40, or each of the object carriers 30. As described above, this is done with the aid of the camera and the computer system 7, it being again preferable to combine sub-images so that the object carriers 30 are respectively imaged fully.

The microscope stage 3 is configured to receive a plurality of object carrier means, so that the object carrier means 30 can be arranged next to one another on the microscope stage 3 and can be moved into the imaging region. The microscope stage 3 furthermore comprises means for aligning the object carriers 30 with respect to the microscope stage 3 and therefore also with respect to one another, and for holding them on the microscope stage 3.

The generated images 20 are evaluated by the image processing means in the evaluation step 210 with the aid of a predetermined rule set 240, 240', in order to identify structures recurring in the images. It is possible for the rule set 240,

240' to be configured so that a predetermined structure is identified as the recurring structure. As an additional condition in this case, it is necessary that the structure can be identified in at least two, but preferably all images 20. It is furthermore necessary to ensure that the recurring structures of different images 20 can be assigned uniquely to one another. Structures which occur at most once in each of the images 20 are therefore suitable in particular. This requirement, moreover, can generally always be fulfilled with an increasing degree of complexity of the structures. A region is respectively selected for the images on the basis of the identified recurring structures, the selected regions of the different images 20 being assigned to one another as described above. In the method, it is also possible to select a plurality of regions for an image.

Characteristic geometrical quantities are in turn determined for the selected regions in the calculation step 220. These characteristic quantities in particular contain the position of these images with respect to the microscope stage 3. A working region for the subsequent processing steps is therefore defined by the regions thus defined and characteristic geometrical quantities thus determined.

If at least three positions are defined for the recurring structures in the individual sections 40, it is furthermore possible to calculate a transformation matrix with the aid of these positions, which takes into account at least a displacement or rotation but preferably also a deformation of the sections 40 which are arranged on object carrier means 30 next to one another on the microscope stage. The transformation matrix makes it possible to convert position specifications for one of the sections 40 into position specifications of another section 40. The transformation matrix is respectively defined between two of the sections 40. In the present case, the transformation matrix is therefore determined for each pair of sections or the transformation matrix is respectively determined with respect to a section used as a reference section.

Image correction of the images 20 is performed on the basis of the transformation matrix in the image correction step 240. This is done by applying the transformation matrix, which is determined with respect to a reference image, to each image 20 other than this reference image.

The subsequent steps 110, 120 and 130 correspond to the method described above with the aid of FIG. 3, although the imaging step is omitted and the images 20 corrected in the correction step 240 are evaluated in the evaluation step 110. It is again possible to select regions for cutting and/or catapulting automatically with the aid of the predetermined or correspondingly defined rule sets 140, 140', or to select objects or regions for cutting and/or catapulting manually with the aid of a section curve 24 and/or target point 25 marked in the image via the input means 9, 10 of the computer system.

The characteristic geometrical quantities obtained in this way then again processed in the form of a list by the control means in the control signal generation step 130.

FIGS. 8A, 8B, 8C and 8D respectively show an image 20 of a section 40 of the type represented in FIG. 6. The procedure for identifying the recurring structures will be explained by way of example below with the aid of these images 20.

It can be seen that on the left-hand side in the images 20, there is a structure which comprises two further structures lying in it. These structures can thus be assigned to a subordinate hierarchy level with respect to the structure comprising them. In order to evaluate the images 20 a rule set is now used, which recognises that a structure with smaller round structures contained in it is present in each of the images 20. There is furthermore only one such structure, so that these structures of the images 20 can be assigned uniquely to one another.

Figure 8A:
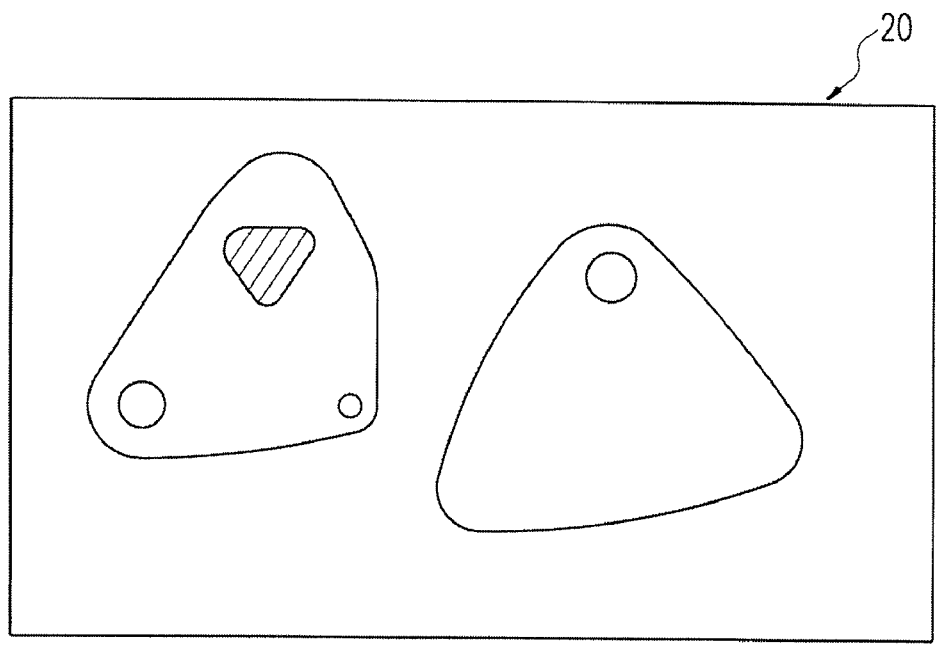
FIGS. 8A and 8B show an image of a section through a material, structures being emphasised by respectively different selective marking, FIGS. 8C and 8D respectively show a further section through the material of FIGS. 8A and 8B, a region whose determined characteristic geometrical quantities are represented having respectively being selected.
Figure 8B:
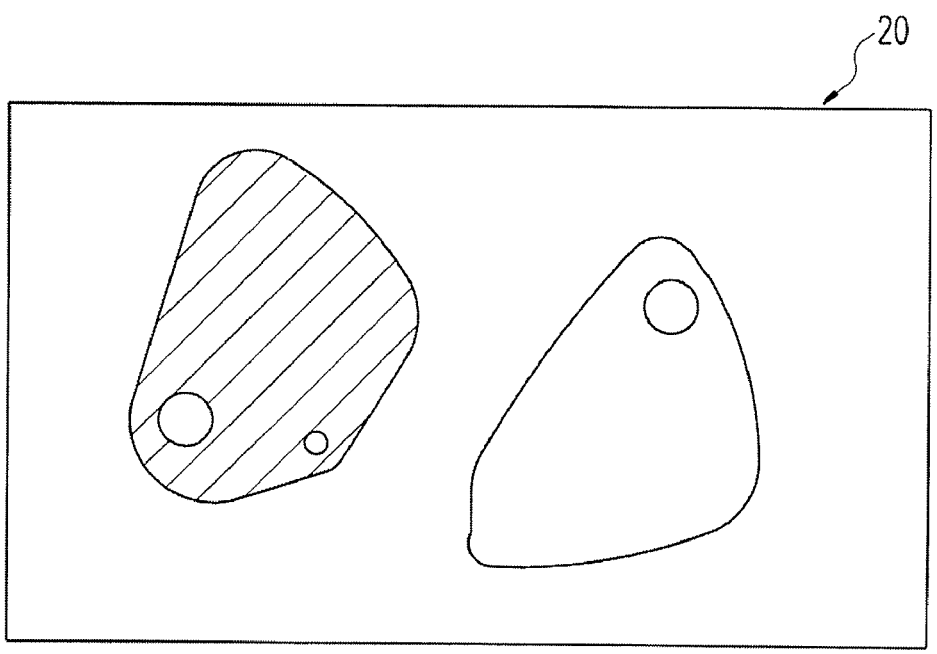

It can furthermore be seen in FIGS. 8A and 8B that further structures have been emphasised in the images 20 by means of staining. A different selective staining has respectively been carried out for the image 20 of FIG. 8A and the image 20 of FIG. 8B. Such selective dyes are well known in microbiology and may, for example, be carried out by means of haematoxylin/eosin for staining cells and cell nuclei. Such colouration has been carried out with different dyes for the images 20 represented in FIGS. 8A and 8B. Respectively different colourations that emphasise structures are obtained, which is illustrated by shading in FIGS. 8A and 8B.

The example shown is selected in such a way that identification of structures with the requisite statistical reliability is not yet possible with the aid of a single staining. But since allocation of regions between the individual sections 40 is possible owing to the recurring structures, the additional information obtained by the selective staining in the images 20 of FIGS. 8A and 8B can be combined so as to greatly increase the statistical reliability of the identification of structures. In the example shown, the structure represented on the left-hand side of the images 20 can be selected as a working region in the images of FIGS. 8C and 8D by means of the structures emphasised by colouration, on the basis of a rule set configured therefor.

Figure 8C:
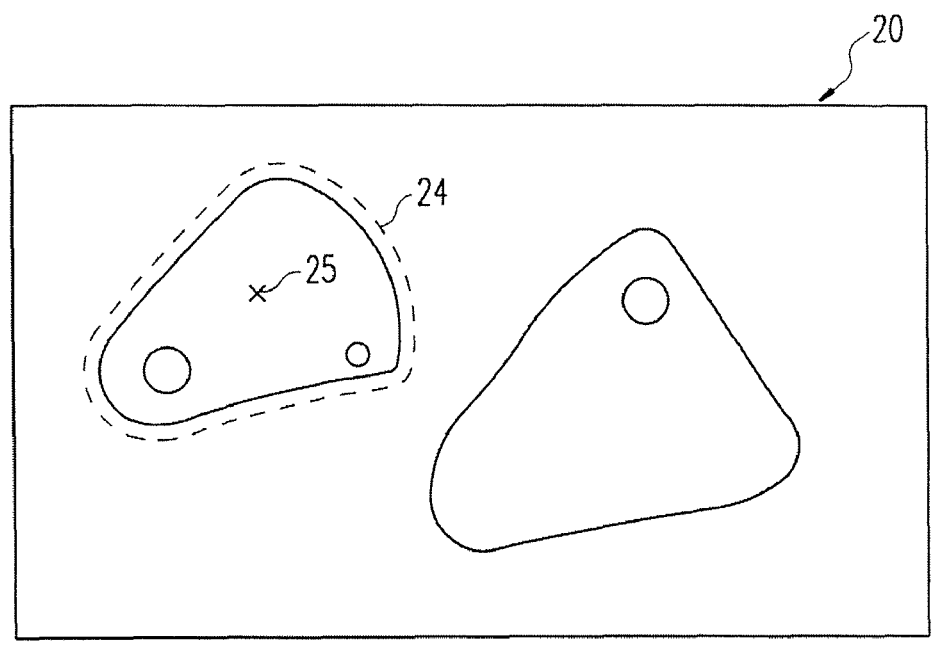
Figure 8D:
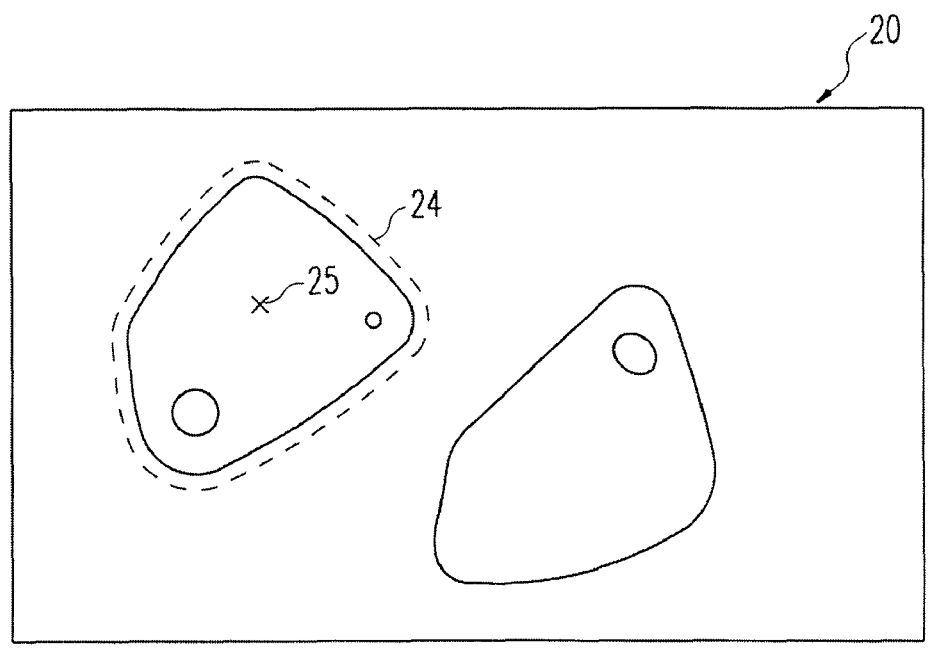

The selected region is represented in FIGS. 8C and 8D, respectively with the characteristic geometrical quantities determined for it in the form of a section curve 24 and a target point 25. As already described above, this region can now be cut out from the material along the section curve 24 and catapulted to the collection device 2 by a laser shot at the target point 25. This means that the region previously selected as a working region has been selected integrally as a region for cutting and/or catapulting. As an alternative, it would also have been possible to select one or more regions inside the working region for cutting and/or catapulting, on the basis of the method described with the aid of FIG. 3. This could, for example, involve the round structures contained in it.

In FIGS. 8A, 8B, 8C and 8D, it is conceivable that changes of the structures contained therein may occur between the various sections 40. This is partly attributable to the fact that the sections 40 are taken in different section planes displaced in a parallel fashion. Since a three-dimensional structure of the material typically changes in a direction perpendicular to the section planes, there are therefore also changes of the structures which are caused in the sections by this three-dimensional structure.

Further changes of the structures, moreover, may result from the fact that displacements, rotations or deformations of the material take place when generating the sections 40 or arranging the sections 40 on the object carrier means 30. In order to process the material on the various sections 40, it is desirable to correct these displacements, rotations or deformations. To this end a transformation matrix is determined, which converts position specifications for one of the sections 40 into position specifications for another section 40 and vice versa.

Figure 9A:
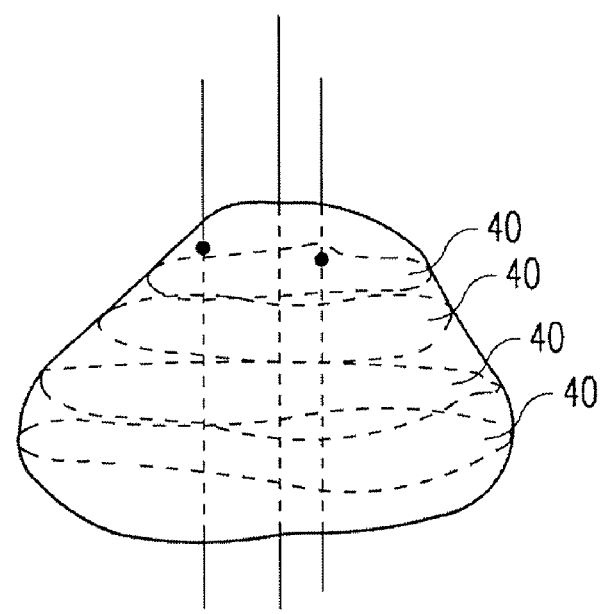
FIGS. 9A and 9B illustrate a method for artificially inducing a recurring structure in parallel sections through a material.

A procedure which makes it possible to determine the transformation matrix will now be explained with the aid of FIGS. 9A and 9B. FIG. 9A schematically shows a perspective representation of a biological material. It is a three-dimensional structure, for example a tissue sample. As indicated by the broken line, sections 40 aligned parallel with a thickness of a few micrometres are taken from the material. To this end, for example, the material is embedded in a paraffin block or frozen as a cryopreparation.

Before generating the sections, as schematically represented in FIG. 9A, three hole regions are made in the material.

These hole regions then extend in a direction which is aligned essentially perpendicularly to the plane of the parallel sections 40 to be taken. In the plane of these sections 40, the hole regions respectively define a well-defined geometrical structure, for example a right-angled triangle.

The hole regions may be made in different ways depending on the nature and consistency of the material, for example by punching, piercing or boring. A specially adapted tool may in particular be used for this, which can generate these hole regions with a well-defined geometry.

Figure 9B:
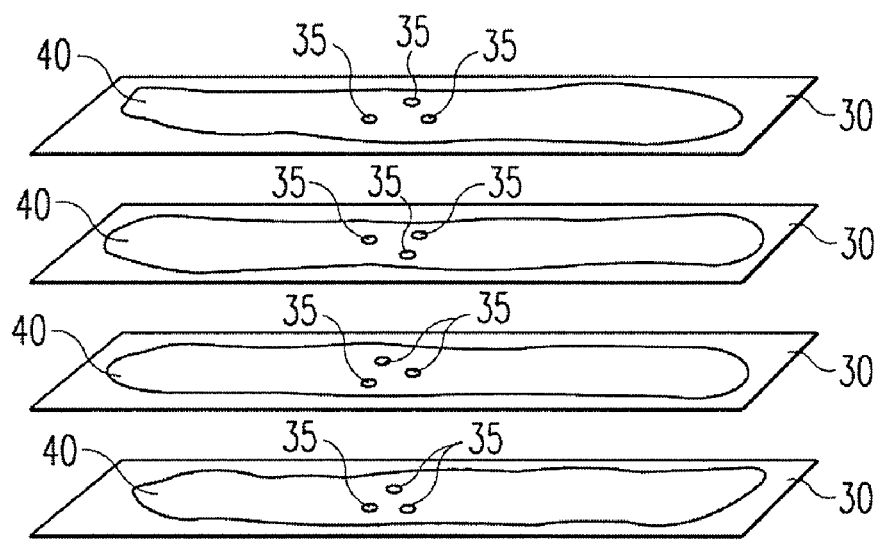

FIG. 9B shows a perspective representation of object carrier means 30 with sections 40 arranged on them, which respectively comprise the hole regions 35 made in the way described above. The hole regions 35 define a structure recurring in each of the sections. This recurring structure may be used, in the way already described above, to identify regions in images of the sections which were next to one another in the individual undivided material. By means of the hole regions 35, this is possible even if the material itself does not comprise any structure which could lead to a significant recurring structure in the sections 40.

Three reference points are furthermore defined by the three hole regions in the sections 40, or the images 20 of them. With the aid of these three reference points, it is possible to define the transformation matrix between the images 20 of two sections 40 in each case. This in particular exploits the fact that the hole regions 35 have defined a well-defined geometrical structure, for example a right-angled triangle, in the section planes of the original undivided material.

It is particularly advantageous for the three hole regions 35 to be made in the material so as to provide a non-rotationally symmetric structure, for example a right-angled triangle. In this way, it is possible to uniquely determine the orientation of the section 40 in the image 20 relative to another of the images 20.

The hole regions 35 or reference points are found by the automatic evaluation of the images 20 of the sections as described above. In this case, however, a rule set is used which is specially adapted for finding the hole regions 35. Again, it is nevertheless possible to select the hole regions 35 manually. The use of hole regions 35 in order to generate the recurring structure, or define the reference points, offers in particular the advantage that they typically have a high contrast in the images 20 and are therefore easy to identify. This means that the rule set used for finding the hole regions can have a simple structure, or that the user's workload for manually selecting these regions is comparatively low.

Figure 10:
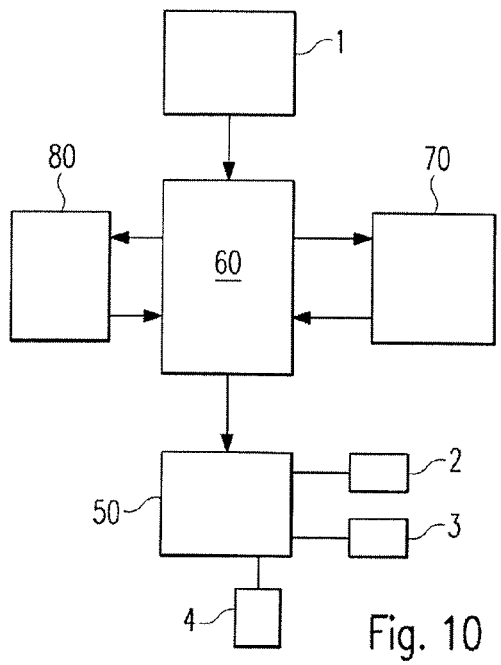
FIG. 10 shows the schematic structure of a control system according to one exemplary embodiment of the present invention.

FIG. 10 represents a control system schematically in the form of a block diagram. The control system is suitable in particular for automatically controlling the method steps explained in the context of the device for processing the biological material as described above. The control system is implemented by corresponding hardware and/or software modules in a computer system 7. The control system comprises storage means 60, image processing means 70 and data processing means 80. The image processing means 70 and data processing means 80 are configured separately in the embodiment represented, although they may also be embodied in a common functionality, for example a main processor of the computer system 7. The control system comprises storage means 60, which are used for storing the images 20 in the digital format in them. Furthermore, the characteristic geometrical quantities determined in the scope of the method described above, for example the section curves 24 and target points 25, are also stored in the form of lists. The control system furthermore comprises control means 50, which generate control signals on the basis of the stored characteristic geometrical quantities. These control signals are fed via corresponding interfaces to the collection device 2, the microscope 3 and the laser device 4. The control system is furthermore provided with interface means for imaging means so that the video signal of the camera of the microscope 1 can be recorded, and the images 20 can be generated on the basis of thereof in the format suitable for the further evaluation.

It is furthermore possible to arrange the image processing means 70 and/or the data processing means 80 externally with respect to the computer system 7, in which case it is possible in particular to carry out the evaluation of the images 20 in a separate computer cluster which is connected to the computer system via a network. In this way the evaluation of the images 20, which demands comparatively high resources, can be performed externally so that the load on the computer system 7 is reduced and resources are therefore released for the control functions.

The invention claimed is:

1. A method for processing a material, wherein the material is located on a carrier, and wherein, by irradiation with a laser beam, the material is cut and/or an object of the material is transferred from the carrier to a collection device, comprising the following steps:
   generating an image of at least a part of the material on the carrier,
   automatically evaluating the image in order to identify predetermined structures in the image,
   automatically selecting a region of the image on the basis of the identified structures,
   determining characteristic geometrical quantities of the selected region, and
   generating control signals for automatically cutting the material and/or transferring the object on the basis of the characteristic geometrical quantities of the selected region, wherein characteristic geometrical quantities of the selected region comprise a circumferential line of the selected region which is defined with respect to the carrier, wherein the characteristic geometrical quantities of the selected region comprise a section curve which is calculated on the basis of the circumferential line of the selected region.

2. The method according to claim 1,
   wherein the automatic evaluation of the image is performed on the basis of contrast information of the image.

3. The method according to claim 1,
   wherein the automatic selection of the region of the image is performed on the basis of the identified structures contained in the region.

4. The method according to claim 1,
   wherein the identification of structures in the image is performed on the basis of relationships of the structures to one another.

5. The method according to claim 1,
   wherein the automatic evaluation of the image is performed on the basis of a rule set which can be selected from a group of predetermined rule sets.

6. The method according to claim 1,
   wherein the characteristic geometrical quantities of the region comprise a position of the selected region on the carrier.

7. The method according to claim 1,
   wherein the section curve is separated from the circumferential line of the selected region by at least a predetermined distance and encloses the circumferential line of the selected region.

8. The method according to claim 7,
wherein the predetermined distance is selected depending on the identified structures.

9. The method according to claim 1,
wherein an adjustment device is provided for inducing a relative movement between the carrier and the laser beam,
the adjustment device is controlled and adjusted by an adjustment control signal, and
the adjustment control signal of the adjustment device is generated on the basis of the section curve, so that the laser beam is moved along the section curve during the automatic cutting.

10. The method according to claim 9,
wherein the characteristic geometrical quantities of the selected region comprise a target point, and
the control signal of the adjustment device is generated on the basis of this target point, so that the laser beam is aimed at the target point for the automatic transfer and the object is transferred from the carrier to the collection device when the laser beam is subsequently activated by a corresponding control signal.

11. The method according to claim 1,
wherein the generation of control signals for automatically cutting the material and/or transferring the object comprises automatic determination of control parameters of a laser light source for generating the laser beam.

12. The method according to claim 1,
wherein the material is arranged on an object carrier means, and essentially the entire object carrier means is imaged when generating the image.

13. The method according to claim 1,
wherein a plurality of sub-images, which are respectively obtained by relative movements of the carrier with respect to a receiving means of an imaging means, are combined when generating the image.

14. The method according to claim 13,
wherein the sub-images are generated in such a way that at least one overlap region between the sub-images is formed when the sub-images are combined to form the image.

15. The method according to claim 14,
wherein structures corresponding to one another are identified in the at least one overlap region by evaluation of the overlapping sub-images, and wherein the sub-images are aligned on the basis of these structures for their combination.

16. The method according to claim 1,
wherein a further image is generated after the automatic cutting of the material,
the further image is automatically evaluated in order to identify therein a predetermined structure in the form of an incomplete section line around the selected region, and
when an incomplete section line has been identified, a section curve is determined in order to complete the incomplete section line, on the basis of which control signals are generated for re-cutting the material.

17. The method according to claim 1,
wherein a plurality of regions are automatically selected,
the characteristic geometrical quantities of each selected region are stored, and
the control signals for automatically cutting the material and/or transferring the object are respectively generated on the basis of the stored characteristic geometrical quantities of the selected regions.

18. The method according claim 1,
wherein additionally manual selection of regions is possible, and
the characteristic geometrical quantities of the manually selected regions are stored in a same format as those of the automatically selected region.

19. The method according to claim 18,
wherein the stored characteristic geometrical quantities are successively processed in the form of a list for automatically cutting the material and/or transferring the object.

20. A method for processing a material, wherein the material is located on a carrier, wherein, by irradiation with a laser beam, the material is cut and/or an object of the material is transferred from the carrier to a collection device, wherein the material is divided into a plurality of parts, and the method comprising the following steps:
respectively generating an image for each of the parts of the material,
automatically evaluating the images in order to identify recurring structures in the images,
automatically selecting a region of the image of at least a part of the material on the basis of the identified structures, and
cutting the material in the selected region and/or transferring the object of the material from the selected region.

21. The method according to claim 20,
wherein the automatic evaluation of the images, in order to identify structures recurring in the images, is performed on the basis of contrast information of the images.

22. The method according to claim 20,
wherein the identification of the recurring structures in the images is performed on the basis of relationships of the structures to one another.

23. The method according to claim 20,
wherein the automatic evaluation of the images is performed on the basis of a rule set which can be selected from a group of predetermined rule sets.

24. The method according to claim 20,
wherein the automatic selection of the region in at least one of the images is performed on the basis of the identified structures contained in the region.

25. The method according to claim 20,
wherein selective marking of structures is performed for at least a part of the material.

26. The method according to claim 25, wherein
the selective marking is performed using a dye.

27. The method according to claim 25,
wherein the cutting and/or transfer of the object from the selected region is performed in a part of the material for which no selective marking of structures has been carried out.

28. The method according to claim 20,
wherein suitable structures of the material are used as the recurring structures.

29. The method according to claim 20,
wherein the material is divided into a plurality of essentially parallel sections, each of which forms one of the parts of the material.

30. The method according to claim 29,
wherein before generating the parallel sections, the material is provided with a marking which leads to a recurring structure in each of the sections.

31. The method according to claim 30,
wherein the marking is carried out using three hole regions, which are made in the material in a direction essentially extending perpendicularly to the planes of the parallel sections.

32. The method according to claim 29,
wherein the recurring structures respectively define at least three positions in at least two of the sections.

33. The method according to claim 32,
wherein reference points with respect to the carrier are determined on the basis of the at least three positions in one of the sections, and the reference points are correlated with correspondingly determined reference points of another of the sections in order to determine a transformation matrix, which allows for position specifications of the one section and position specifications of the other section to be converted into one another.

34. The method according to claim 33, wherein the transformation matrix takes into account displacements, rotations or deformations of the sections relative to one another.

35. The method according to claim 20, further comprising the following steps for at least one of the parts of the material:
automatically evaluating the image of this part of the material, in order to identify predetermined structures in the image,
automatically selecting a region as a function of the identified structures,
determining characteristic geometrical quantities of the selected region, and
generating control signals for automatically cutting the material and/or transferring the object on the basis of the characteristic geometrical quantities of the selected region.

36. A control system for a device for processing a material located on a carrier, wherein the device comprises a laser light source for generating a laser beam to cut the material and/or transfer an object of the material to a collection device by irradiation with the laser beam, and imaging means for generating at least one image of at least a part of the material, and the control system comprises:
control means for automatically controlling the laser light source and for automatically controlling adjustment means to induce a relative movement between the laser beam and the material,
image processing means for automatically evaluating the at least one image in order to identify structures therein, and
data processing means which are configured to select a region of the image automatically on the basis of the identified structures, wherein characteristic geometrical quantities of the selected region comprise a circumferential line of the selected region which is defined with respect to the carrier, and wherein the characteristic geometrical quantities of the selected region comprise a section curve which is calculated on the basis of the circumferential line of the selected region.

37. The control system according to claim 36,
wherein the data processing means are configured to determine characteristic geometrical quantities of the selected region of the image.

38. The control system according to claim 37,
wherein the control means are configured to generate control signals for automatically cutting the material and/or transferring the object on the basis of the characteristic geometrical quantities of the selected region of the image.

39. A device for processing a material located on a carrier with a laser beam, comprising:
a laser light source for generating a laser beam to cut the material located on the carrier and/or transfer an object of the material to a collection device by irradiation with the laser beam,
imaging means for generating at least one image of at least a part of the material, and
a control system,
wherein the control system comprises:
control means for automatically controlling the laser light source and for automatically controlling adjustment means to induce a relative movement between the laser beam and the material,
image processing means for automatically evaluating the at least one image in order to identify structures therein, and
data processing means which are configured to select a region of the image automatically on the basis of the identified structures, wherein characteristic geometrical quantities of the selected region comprise a circumferential line of the selected region which is defined with respect to the carrier, and wherein the characteristic geometrical quantities of the selected region comprise a section curve which is calculated on the basis of the circumferential line of the selected region.

40. The device according to claim 39,
wherein the device is a laser microscope system.

41. The device according to claim 39, wherein the device is a laser microdissection system.

42. A non-transitory computer program product having a program code which is configured to carry out on a computer system a method comprising the following steps:
generating an image of at least a part of a material located on a carrier,
automatically evaluating the image in order to identify predetermined structures in the image,
automatically selecting a region of the image on the basis of the identified structures,
determining characteristic geometrical quantities of the selected region, and
generating control signals for automatically cutting the material and/or transferring an object of the material to a collection device by irradiation with a laser beam, wherein the characteristic geometrical quantities of the selected region comprise a circumferential line of the selected region which is defined with respect to the carrier, and wherein the characteristic geometrical quantities of the selected region comprise a section curve which is calculated on the basis of the circumferential line of the selected region.

43. A non-transitory computer program product having a program code which is configured to carry out on a computer system a method comprising the following steps:
respectively generating an image for each part of a material which is divided into a plurality of parts,
automatically evaluating the images in order to identify recurring structures in the images,
automatically selecting a region of the image of at least a part of the material on the basis of the identified recurring structures, and
generating control signals for automatically cutting the material and/or transferring an object of the material to a collection device by irradiation with a laser beam.

44. A control system for a device for processing a material located on a carrier, wherein the device comprises a laser light source for generating a laser beam to cut the material and/or transfer an object of the material from the carrier to a collection device by irradiation with the laser beam, and imaging means for generating at least one image of at least a part of the material, and the control system comprises units, wherein the units include at least one of hardware and a computer executing software stored on a non-transitory computer-readable storage medium storing software modules therein, the units including:

a control unit constructed to automatically control the laser light source and to automatically control an adjustment unit to induce a relative movement between the laser beam and the material;

an image processing unit constructed to automatically evaluate the at least one image in order to identify structures therein;

a data processing unit constructed to select a region of the image automatically on the basis of the identified structures;

an image generating unit constructed to respectively generate an image for each of the parts of the material;

an evaluating unit constructed to automatically evaluate the images in order to identify recurring structures in the images;

a selecting unit constructed to automatically select a region of the image of at least a part of the material on the basis of the identified structures; and cutting unit constructed to cut the material in the selected region and/or transfer the object of the material from the selected region.

45. A device for processing a material with a laser beam, comprising:

a laser light source for generating a laser beam to cut the material and/or transfer an object of the material to a collection device by irradiation with the laser beam, imaging unit constructed to generate at least one image of at least a part of the material, and a control system, wherein the control system comprises units, wherein the units include at least one of hardware and a computer executing software stored on a non-transitory computer-readable storage medium storing software modules therein, the units including:

a control unit constructed to automatically control the laser light source and constructed to automatically control an adjustment unit to induce a relative movement between the laser beam and the material, an image processing unit constructed to automatically evaluate the at least one image in order to identify recurring structures in the images, and an evaluating unit constructed to automatically evaluate the images in order to identify recurring structures in the images;

a selecting unit constructed to automatically select a region of the image of at least a part of the material on the basis of the identified structures; and a cutting unit constructed to cut the material in the selected region and/or transfer the object of the material from the selected region.

* * * * *